United States Patent [19]

Burstein et al.

[11] E Re. 28,502

[45] Reissued Aug. 5, 1975

[54] INTRAMEDULLARY ROD

[75] Inventors: Albert H. Burstein, Shaker Heights, Ohio; William C. Allen, Gainesville, Fla.

[73] Assignee: The Sampson Corporation, Pittsburgh, Pa.

[22] Filed: May 6, 1974

[21] Appl. No.: 467,147

Related U.S. Patent Documents

Reissue of:

[64] Patent No.: 3,783,860
Issued: Jan. 8, 1974
Appl. No.: 301,473
Filed: Oct. 27, 1972

[52] U.S. Cl. ..... 128/92 BC
[51] Int. Cl. ..... A61f 5/04
[58] Field of Search ..... 128/92 BC, 92 BB, 92 BA, 128/92 B, 92 R, 92 EC, 92 D; 85/13, 19

[56] References Cited

UNITED STATES PATENTS

| | | | |
|---|---|---|---|
| 2,236,804 | 4/1941 | Miller | 85/19 |
| 2,251,202 | 7/1941 | Purtell | 85/19 |
| 2,412,517 | 12/1946 | Klein | 85/19 |
| 2,490,364 | 12/1949 | Livingston | 128/92 BB |
| 2,496,126 | 1/1950 | Haboush | 128/92 BA |

OTHER PUBLICATIONS

Down Bros. and Mayer & Phelps, Ltd., Surgical Catalogue, p. G20, 1966.

Journal Bone & Joint Surgery, Nov. 1951, page 11.

*Primary Examiner*—Richard A. Gaudet
*Assistant Examiner*—J. Yasko
*Attorney, Agent, or Firm*—Dennison, Dennison, Townshend & Meserole

[57] ABSTRACT

An intramedullary rod for internal fixation of long bone fractures in the form of an elongated hollow tube having longitudinal flutes about the periphery. Each end is [castellated] *formed* to provide [alternate] *a plurality of* sharp cutting surfaces and *an* angled face guide [projections] *means* to facilitate emplacement in the medullary canal.

7 Claims, 5 Drawing Figures

INTRAMEDULLARY ROD

Matter enclosed in heavy brackets [ ] appears in the original patent but forms no part of this reissue specification; matter printed in italics indicates the additions made by reissue.

BACKGROUND OF THE INVENTION

This invention relates generally to a tool for use in orthopedic surgery and more specifically to a new intramedullary rod or nail for use in surgical fracture fixation to maintain the fractured portions of long bones together.

In the field of orthopedic surgery it has become common practice in certain situations to use as a fracture fixation means an elongated nail or rod, commonly known as an intramedullary rod. Such a rod is driven into the narrow cavity or medullary passage longitudinally in a fractured bone after lateral reduction and serves to hold the severed parts thereof in longitudinal alignment incident to knitting and healing of the fracture. Such nails or rods are generally used in treatment of long bone fractures, and, for example, in treatment of the fracture of the femur, the nail or rod is driven percutaneously longitudinally through the tip of the trochanter and into the medullary canal and serves to bridge the point of fracture in the stem on either side thereof.

Intramedullary rods are known in various forms but it has been most satisfactory in obtaining a solid and secure joinder of fractured bones by using a rod which will not twist or turn within the narrow passage of the bone. The ideal function of an intramedullary rod is to hold the proximal and distal fragments of the bone which has been fractured in correct alignment during the process of healing. Several types of loads must be transmitted from the distal to the proximal fragments, these include compression, bending and torsion. The compressive loads are transmitted generally directly through the bone surface, while torsional and bending loads are transmitted at least in part by the intramedullary rod. In order to properly transmit torque, the rod or nail must be capable of tightly gripping both the proximal and distal fragments. Additionally, the nail must be sufficiently rigid to prevent excessive bending at the fracture site.

The current nail designs available on the market today do not accomplish all of the functions necessary in the ideal rod as described above. Among the designs presently available are the Kuntscher, Schneider, and Hansen-Street nails or rods. Several of these designs rely on friction gripping and are of open section design which does not have sufficient torsional rigidity. Ideally, the rod should be of such design and strength as to approach the strength of the healed bone.

SUMMARY OF THE INVENTION

The new intramedullary rod disclosed herein is of generally hollow internal construction and is provided with flutes extending longitudinally on the external surface thereof. A novel [ castellated ] end configuration is provided on each of the ends of the rod providing a guiding-cutting tip to enable the nail to be inserted in the medullary canal with greater facility and to enable the material displaced during insertion of the rod to pass within the rod itself. This construction provides a stronger rod and the most efficient compromise in shape for maximum torsional and bending strength within the confines of bone geometry.

An object of the present invention is to provide an intramedullary nail having a high strength both in bending and in torsion comparable to the strength of the normal femur to thereby make early mobilization practical without fear of bending the nail.

It is a further object of this invention to provide an intramedullary nail having similar end configurations so that the same may be introduced either through the fracture in a retrograde manner or through a proximal insertion over the distal femoral neck.

A further object of this invention is to provide a high strength hollow intramedullary rod having a fluted external surface to allow maximal intramedullary gripping.

Yet a further object of the invention is to provide a cutting surface on the advancing edge of the flutes of an intramedullary rod in order to cut through bone to prevent splitting or wedging.

Another object of this invention is to provide an intramedullary rod that requires only a driver for insertion which may be manufactured in various diameters and lengths.

It is another object of the present invention to provide an intramedullary rod that has the advantage of being able to grip all around the endosteal surface of a bone without completely filling the endosteal volume.

Another object of the invention is to provide an intramedullary rod which requires less force for insertion since material is being cut.

Another object of the invention is the provision of a novel hollow intramedullary rod which is of generally simple construction, is relatively inexpensive to manufacture, and is safe and efficient in use.

The above and other objects and features of the invention will become more apparent from a consideration of the following disclosure.

DESCRIPTION OF THE PREFERRED EMBODIMENT

Figure 3:
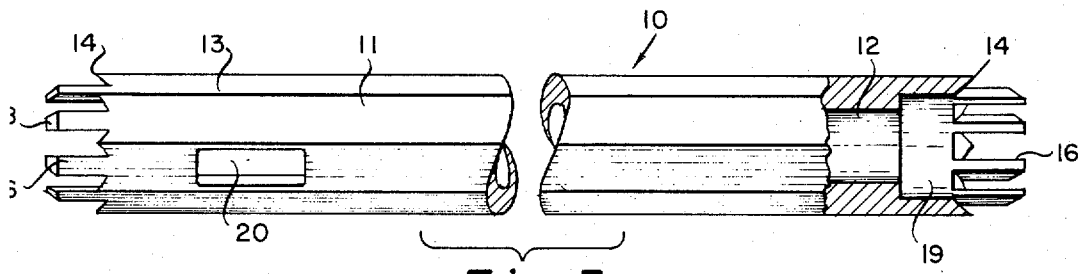
FIG. 3 is a side elevation of the intramedullary rod of the present invention with selected portions shown in cross section.

The intramedullary rod of the present invention is shown generally at 10 and as will be noted from FIG. 3 is preferably in the form of an elongated hollow tube 11 having a cylindrical bore 12 extending longitudinally therethrough. The rod may be formed of any metallic substance compatible with human tissue.

Figure 4:
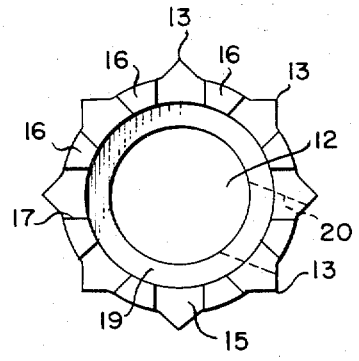
FIG. 4 is an enlarged end view of the intramedullary rod shown in FIG. 3.
Figure 5:
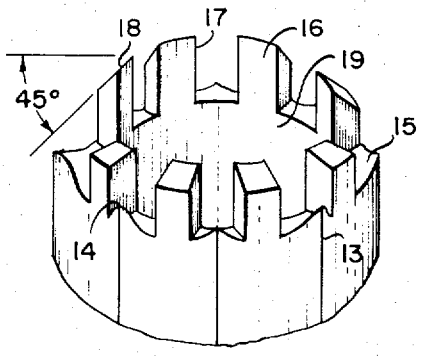
FIG. 5 is an enlarged perspective view of the end portion of the intramedullary rod.

A plurality of longitudinal circumferentially spaced flutes 13 extend about the circumference of the rod and terminate at either end in inwardly sharply sloped cutting points 14. As will be apparent from FIG. 5, the end surface of the cutting points slopes inwardly and downwardly toward the center of the rod resulting in a relatively sharp cutting chisel point construction. Intermediate the flutes 13, the end surface is castellated to provide guiding projections 16. These projections have straight side walls 17 and the end faces thereof slope downwardly and outwardly from the inner surface to the outer face of the rod in a manner opposite to the slope of the cutting point 14. It will be noted that the projections 16 extend longitudinally beyond the points 14. Note the sloping end face 18 which is preferably cut at an angle of approximately 45° from the horizontal as shown in FIG. 5. This end face configuration on projection 16 provides a guiding surface and as will be apparent from a study of FIG. 4, the outer edge of the guiding projections is spaced radially inwardly from the outermost edge of the cutting points 14.

Each end of the hollow tube 11 is preferably provided with a recessed counterbore 19 which, if desired, may be internally threaded for reception of a conventional extractor. A preferred extractor arrangement includes provision of an extractor slot 20 formed intermediate to adjacent flutes and taking the form of a rectangular through slot. Conventional extraction means known in the art may be inserted through the opening or slot 20 to aid in removal of the intramedullary rod.

Figure 2:
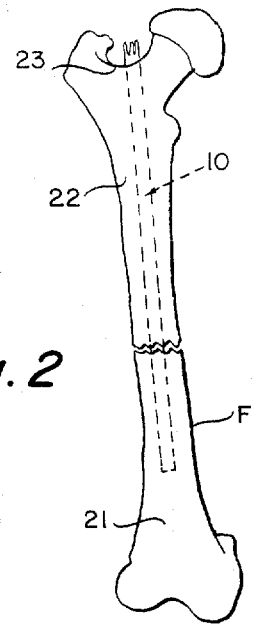
FIG. 2 is a side elevation of a fractured human femur showing the intramedullary rod of the present invention in position in the medullary canal.

A typical fracture of a femur F is shown in FIG. 2 wherein the distal end of the bone is shown at 21 and the proximal end at 22. In order to insert the rod, under surgical conditions an incision is made adjacent to the hip exposing the trochanter and the tissues may be held retracted by means of conventional retractors R. A reamer or drill may then be applied to provide a longitudinal passageway through the bone passing through both dense compact cortical bone as well as cancellous bone.

Figure 1:
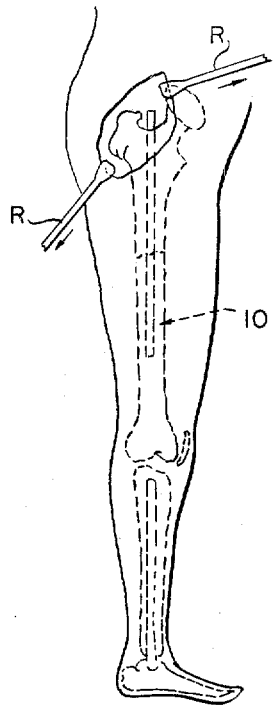
FIG. 1 is a side elevation of the right human lower limb showing a portion thereof incised and the opening retracted to show a portion of the trochanter and neck of the femur with the remainder of the bones of the leg and the intramedullary rod shown in phantom.

The intramedullary rod is then inserted into the medullary canal through the trochanter 23 as shown in FIGS. 1 and 2, and with application of percussive force the rod is passed downwardly extending into the distal end 21 of the bone. The cutting points 14 on the flutes 13 serve to cut into the wall of the hole formed by the reamer or drill. The guiding surfaces 18 on the castellated projections 16 guide the intramedullary rod and prevent it from cutting out of the bone. This particular end arrangement also serves to channel loose material and extrude the same into the hollow internal portion 12 of the rod 11. The material of the bone which is cut by the points 14 being generally cortical will then pass into the cavity 12. The flutes provide a means for gripping the bone both proximal and distal to the fixation site. This will allow better transmission of torque across the generally torsionally unstable fixation. The mechanical locking provided is a superior method to the frictional system as employed in the prior art Kuntscher rods and provides a better result than the self-broaching technique of the Schneider nail since there is less chance of the rod cutting through the bone due to the presence of the guiding surfaces provided herein. An additional advantage is that less force is needed for insertion since less material is being cut.

The present intramedullary rod has the advantage of being able to grip all around the endosteal surface of the bone without completely filling the endosteal volume since the nail is hollow. The hollow structure presents the most efficient compromise in shape for maximum torsional and bending strength within the confines of bone geometry.

It is also contemplated that the hollow feature will permit insertion of viscous fluids into the distal segment of the bone. Methylmethacrylate has recently been used in such procedures and may be applied through the proximal end which has been exposed. Utilizing such a technique, the rod may serve as a permanent bone bridge in cases where nonunion persists. Generally, however, after knitting of the bone structure, the rod 10 is drawn out of the marrow passage.

It is apparent that the strength and rigidity of the proposed rod may be regulated by design parameters relative to the inside and outside diameters and length. Accordingly, a large diameter rod may be made without excessive rigidity which might produce delayed union of the fracture.

After the bone portions have knit and healed, a subsequent operation may be performed to expose the extractor slot 20 for application of a conventional extractor tool to withdraw the rod from the medullary canal. Alternatively, the recessed counterbore 19 may be provided with internal threads for reception of a threaded insert for this purpose.

It will be apparent that both ends of the rod have similar configurations and therefore the rod may be introduced either through the fracture in a retrograde manner or through a proximal insertion over the distal femoral neck. During insertion, the advancing edge of the flutes 13 and their associated cutting points 14 cut through the bone so that unlike prior art nails splitting of the shaft or wedging of the rod so that it sticks is clearly minimized.

While we have described our intramedullary rod in specific detail, it will be apparent that the same may be modified or varied in many respects without departing from the invention, and therefore other variations and alterations may come within the scope of the following claims.

We claim:

1. An intramedullary rod for fracture fixation comprising an elongated hollow tube open at each end and hollow throughout, said tube having at least one end surface castellated and defined by a plurality of longitudinal projections, a first group of said projections having pointed, relatively sharp, end surfaces defining cutting faces, a second group of said projections being spaced alternately with said first set of projections and having angled flat end surfaces defining guiding faces.

2. An intramedullary rod as defined in claim 1, wherein each end surface of said tube is castellated.

3. An intramedullary rod as defined in claim 1, wherein said tube is provided with a plurality of longitudinally extending elongated flutes about the external surface thereof.

4. An intramedullary rod as defined in claim 3, wherein the flutes extend longitudinally and join the first group of projections.

5. An intramedullary rod for fracture fixation comprising an elongated tube open at each end and hollow throughout, a plurality of longitudinally extending elongated flutes about the external surface of said tube, on at least one end face of said tube the flutes being sharply sloped inwardly at an acute angle to define a plurality of cutting surfaces, the tube portions intermediate said flutes having their end surfaces on said one end face sloped gradually inwardly at an obtuse angle to define a plurality of guide surfaces.

6. An intramedullary rod as defined in claim 5 and including a rectangular slot in the tube wall surface for reception of a retraction tool.

*7. An intramedullary rod for fracture fixation comprising an elongated tube open at each end and hollow throughout, a plurality of longitudinally extending elongated flutes about the external surface of said tube, on at least one end face of said tube the flutes being sharply sloped inwardly at an acute angle to define a plurality of cutting surfaces, guide means extending axially from said one end face beyond said cutting surfaces and having a guide surface sloped gradually inwardly at an obtuse angle.*

* * * * *